(12) United States Patent (10) Patent No.: US 7,758,882 B2
Roeder et al. (45) Date of Patent: Jul. 20, 2010

(54) COMPOSITE BIOMATERIAL INCLUDING ANISOMETRIC CALCIUM PHOSPHATE REINFORCEMENT PARTICLES AND RELATED METHODS

(75) Inventors: Ryan K. Roeder, Granger, IN (US); Charles H. Turner, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 991 days.

(21) Appl. No.: 10/182,823

(22) PCT Filed: Jan. 31, 2001

(86) PCT No.: PCT/US01/03219

§ 371 (c)(1),
(2), (4) Date: Jul. 31, 2002

(87) PCT Pub. No.: WO01/54746

PCT Pub. Date: Aug. 2, 2001

(65) Prior Publication Data

US 2003/0031698 A1 Feb. 13, 2003

Related U.S. Application Data

(60) Provisional application No. 60/179,238, filed on Jan. 31, 2000.

(51) Int. Cl.
*A61F 2/28* (2006.01)
(52) U.S. Cl. .................. 424/426; 424/424; 424/425
(58) Field of Classification Search ................ 424/484, 424/486, 422, 423, 426
See application file for complete search history.

(56) References Cited

U.S. PATENT DOCUMENTS

| | | | |
|---|---|---|---|
| 4,321,042 A | 3/1982 | Scheicher | |
| 4,503,157 A | 3/1985 | Hatahira | |
| 4,518,430 A | 5/1985 | Brown et al. | |
| 4,612,053 A | 9/1986 | Brown et al. | |
| 4,880,610 A | 11/1989 | Constantz | |
| 5,017,627 A * | 5/1991 | Bonfield et al. | 523/115 |
| 5,034,059 A | 7/1991 | Constantz | |

(Continued)

FOREIGN PATENT DOCUMENTS

DE 29 17 037 B 4/1980

(Continued)

OTHER PUBLICATIONS

Roeder et al, "Hydroxyapatite Whiskers Provide Improved Mechanical Properties in reinforced Polymer Composites", Journal of Biomedical Materials research Part A, vol. 67A, Issue 3, pp. 801-812, Oct. 16, 2003.*

(Continued)

*Primary Examiner*—Carlos A Azpuru
(74) *Attorney, Agent, or Firm*—Leydig, Voit & Mayer, Ltd.

(57) ABSTRACT

Composite biomaterials (e.g., for use as orthopedic implants), as well as methods of preparing composite biomaterials, are disclosed. The composite biomaterial includes a matrix (e.g., a continuous phase) comprising a thermoplastic, a calcium phosphate composition that is curable in vivo, or combinations thereof. The composite biomaterial also includes an isometric calcium phosphate reinforcement particles which are dispersed within the matrix.

65 Claims, 3 Drawing Sheets

U.S. PATENT DOCUMENTS

| | | |
|---|---|---|
| 5,047,031 A | 9/1991 | Constantz |
| 5,053,212 A | 10/1991 | Constantz et al. |
| 5,129,905 A | 7/1992 | Constantz |
| 5,164,187 A | 11/1992 | Constantz et al. |
| 5,178,845 A | 1/1993 | Constantz et al. |
| 5,179,993 A | 1/1993 | Bak et al. |
| 5,188,670 A | 2/1993 | Constantz |
| 5,227,147 A | 7/1993 | Yoshimura et al. |
| 5,231,169 A | 7/1993 | Constantz et al. |
| 5,279,831 A | 1/1994 | Constantz et al. |
| 5,336,264 A | 8/1994 | Constanz et al. |
| 5,455,231 A | 10/1995 | Constantz et al. |
| 5,496,399 A | 3/1996 | Ison et al. |
| 5,569,442 A | 10/1996 | Fulmer et al. |
| 5,571,493 A | 11/1996 | Fulmer et al. |
| 5,580,623 A | 12/1996 | Fulmer et al. |
| 5,650,176 A | 7/1997 | Lee et al. |
| 5,652,056 A | 7/1997 | Pepin |
| 5,658,332 A | 8/1997 | Ducheyne et al. |
| 5,676,976 A | 10/1997 | Lee et al. |
| 5,681,872 A | 10/1997 | Erbe |
| 5,683,461 A | 11/1997 | Lee et al. |
| 5,683,496 A | 11/1997 | Ison et al. |
| 5,683,667 A | 11/1997 | Fulmer et al. |
| 5,697,981 A | 12/1997 | Ison et al. |
| 5,709,742 A | 1/1998 | Fulmer et al. |
| 5,766,618 A | 6/1998 | Laurencin et al. |
| 5,782,971 A | 7/1998 | Constantz et al. |
| 5,783,217 A | 7/1998 | Lee et al. |
| 5,814,681 A | 9/1998 | Hino et al. |
| 5,820,632 A | 10/1998 | Constantz et al. |
| 5,846,312 A | 12/1998 | Ison et al. |
| 5,885,540 A | 3/1999 | Fulmer et al. |
| 5,900,254 A | 5/1999 | Constantz |
| 5,914,356 A | 6/1999 | Erbe |
| 5,939,039 A | 8/1999 | Sapieszko et al. |
| 5,952,010 A | 9/1999 | Constantz |
| 5,962,028 A | 10/1999 | Constantz |
| 5,964,807 A | 10/1999 | Gan et al. |
| 5,964,932 A | 10/1999 | Ison et al. |
| 5,968,253 A | 10/1999 | Poser et al. |
| 5,981,619 A * | 11/1999 | Shikinami et al. ............ 523/113 |
| 6,002,065 A | 12/1999 | Constantz et al. |
| 6,005,162 A | 12/1999 | Constantz |
| 6,013,591 A | 1/2000 | Ying et al. |
| 6,027,742 A | 2/2000 | Lee et al. |
| 6,053,970 A | 4/2000 | Ison et al. |
| 6,083,229 A | 7/2000 | Constantz et al. |
| 6,117,456 A | 9/2000 | Lee et al. |
| 6,132,463 A | 10/2000 | Lee et al. |
| 6,139,578 A | 10/2000 | Lee et al. |
| 6,149,655 A | 11/2000 | Constantz et al. |
| 6,156,428 A | 12/2000 | Gibson |
| 6,201,039 B1 | 3/2001 | Brown et al. |
| 6,214,368 B1 | 4/2001 | Lee et al. |
| 6,240,926 B1 | 6/2001 | Chin Gan et al. |
| 6,254,855 B1 | 7/2001 | Rudin et al. |
| 6,270,562 B1 | 8/2001 | Jia |
| 6,273,916 B1 | 8/2001 | Murphy |
| 6,277,151 B1 | 8/2001 | Lee et al. |
| 6,287,341 B1 | 9/2001 | Lee et al. |
| 6,331,312 B1 | 12/2001 | Lee et al. |
| 6,334,891 B1 | 1/2002 | Constantz et al. |
| 6,379,453 B1 | 4/2002 | Lin et al. |
| 6,383,519 B1 | 5/2002 | Sapieszko et al. |
| 6,522,446 B2 | 2/2003 | Saxe |
| 6,529,312 B1 | 3/2003 | Saxe |
| 6,783,799 B1 * | 8/2004 | Goodson ............... 427/140 |
| 6,987,602 B2 | 1/2006 | Saxe |

FOREIGN PATENT DOCUMENTS

| | | |
|---|---|---|
| DE | 2917037 B | 4/1980 |
| EP | 0 835 668 A1 | 4/1998 |
| WO | WO 97/38676 A1 | 10/1997 |

OTHER PUBLICATIONS

Nakahira et al; "Novel synthesis method of hydroxyapatite whiskers by hydrolysis of α-tricalcium phosphate in mixtures of water and organic solvent," *Journal of the American Ceramic Society*, 82(8), 2029-2032 (Aug. 1999).

Abram et al., "The Influence of Compounding Route on the Mechanical Properties of Highly Loaded Particulate Filled Polyethylene Composites," *Plast. Rubber Process. and Appl.*, 4 [3] 261-269 (1984).

Ambrosio et al., "A Novel Amorphous Calcium Phosphate Polymer Ceramic for Bone Repair: I, Synthesis and Characterization," *J. Biomed. Mater. Res. (Appl. Biomater.)*, 58 [3] 295-301 (2001).

Ascenzi et al., "Orientation of Apatite in Single Osteon Samples as Studied by Pole Figures," *Calif. Tissue Int.*, 29, 101-105 (1979).

Ascenzi et al., "X-ray Diffraction Analysis of Transversal Osteonic Lamellae," *Calif Tissue Int.*, 35, 279-283 (1983).

Beatty et al., "Effect of Microfiller Fraction and Silane Treatment of Resin Composite Properties," *J. Biomed. Mater. Res.*, 40 [1] 12-23 (1998).

Beruto et al., "Use of α-tricalcium Phosphate (TCP) as Powders and as an Aqueous Dispersion to Modify Processing, Microstructure, and Mechanical Properties of Polymethylmethacrylate (PMMA) Bone Cements and to Produce Bone-substitute Compounds," *J. Biomed. Mater. Res.*, 49 [4] 498-505 (2000).

Boeree, et al., "Development of a Degradable Composite for Orthopaedic Use: Mechanical Evaluation of an Hydroxyapatite-polyhydroxybutyrate Composite Biomaterial," *Biomaterials*, 14 [10] 793-796 (1993).

Bonfield, "Composites for Bone Replacement," *J. Biomed. Eng.*, 10, [6] 522-526 (1988).

Bonfield et al., "Hydroxyapatite Reinforced Polyethylene—a Mechanically Compatible Implant Material for Bone Replacement," *Biomaterial*, 2, 185-186 (1981).

Constantz et al., "Skeletal Repair by in Situ Formation of the Mineral Phase of Bone," *Science*, 267, 1796-1799 (1995).

Cowin, "The Mechanical Properties of Cortical Bone and Cancellous Bone Tissue," *Bone Mechanics*, pp. 97-127. Edited by S.C. Cowin, CRC Press, Inc., Boca Raton, FL, (1989).

Doyle et al., In Vitro and In Vivo Evaluation of Polyhyrdroxybutyrate and of Polyhydroxybutyrate Reinforced with Hydroxyapatite, *Biomaterials*, 12 841-847 (1991).

Durucan et al., "Calcium-deficient Hydroxyapatite-PLGA Composites: Mechanical Properties and Microstructural Characterization," *J. Biomed. Mater. Res.*, 51 [4] 726-734 (2000).

Durucan et al., "Low Temperature Formation of Calcium-deficient Hydroxyapatite-PLA/PLGA Composites," *J. Biomed. Mater. Res.*, 51 [4] 717-725 (2000).

Evans et al., "Composite Technology in Load-bearing Orthopaedic Implants," *Biomaterials*, 19 [15] 1329-1342 (1998).

Fu et al., "Polyethylene Toughened by Rigid Inorganic Particles," *Polym. Engl. Sci.*, 32 [2] 94-97 (1992).

Fujishiro et al., "Preparation of Needle-like Hydroxyapatite by Homogeneous Precipitation under Hydrothermal Conditions," *J. Chem. Technol. Biotechnol.*, 57 349-353 (1993).

Greish et al., "An Evaluation of Mechanical Property and Microstructural Development in HAP-Ca Polycarboxylate Biocomposites Prepared by Hot Pressing," *J. Biomed. Mater. Res. (Appl. Biomater.)*, 53 [4]421-429 (2000).

Greish et al., "Characterization of Bioactive Glass-reinforced HAp-polymer Composites," *J. Biomed. Mater. Res.*, 52 [4] 687-694 (2000).

Greish et al., "Characterization of Wollastonite-reinforced HAP-Ca Polycarboxylate Composites," *J. Biomed. Mater. Res.*, 55 [4] 618-628 (2001).

Greish et al., "Formation and Properties of Hydroxyapatite-Calcium Poly(vinyl phosphate) Composites," *J. Am. Ceram. Soc.*, 85 [7] 1738-1744 (2002).

Harper et al., "Flexural and Fatigue Properties of a Bone Cement Based Upon Polyethylmethacrylate and Hydroxyapatite," *J. Mater. Sci.: Mater. Med.*, 6 [12] 799-803 (1995).

Higashi et al., "Polymer-hydroxyapapite Composites for Biodegradable Bone Fillers," *Biomaterials*, 7, 183-187 (1986).

Ignjatovic et al., "Synthesis and Properties of Hydroxyapatite/poly-L-lactide Composite Biomaterials," *Biomaterials*, 20, 809-816 (1999).

Kandori et al., "Texture and Formation Mechanism of Fibrous Calcium Hydroxyapatite Particles Prepared by Decomposition of Calcium-EDTA Chelates," *J. Am. Ceram. Soc.*, 80 [5] 1157-2264 (1997).

Kikuchi et al., "Preparation and Mechanical Properties of Calcium Phosphate/copoly-L-lactide Composites," *J. Mater. Sci. Mater. Med.*, 8, 361-364 (1997).

Knaack et al., "Resorbable Calcium Phosphate Bone Substitute," *J. Biomed. Mater. Res. (Appl. Biomater.)*, 43 [4] 399-409 (1998).

Kobayashi et al., "Bioactive Bone Cement: Comparison of Apatite and Wollastonite Containing Glass-Ceramic, Hydroxyapatite, and $\beta$-Tricalcium Phosphate Fillers on Bone Bonding Strength," *J. Biomed. Mater. Res.*, 42 [2] 2223-237 (1998).

Ladizesky et al., "Fibre Reinforcement of Ceramic/Polymer Composites for a Major Load-Bearing Bone Substitute Material," *Compos. Sci. Technol.*, 58, 419-434 (1998).

Ladizesky et al., "Hydrostatic Extrusion of Polyethylene Filled with Hydroxyapatite," *Polym. Adv. Technol.*, 8 [8] 496-504 (1997).

Ladizesky et al, "Hydroxyapatite/High Performance Polyethylene Fiber Composites for High-Load-Bearing bone Replacement Materials," *J. Appl. Polym. Sci.*, 65 [10] 1865-1882 (1997).

Mickeiwicz et al., "Polymer-calcium Phosphate Cement Composites for Bone Substitutes," *J. Biomed. Mater. Res.*, 61 [4] 581-592 (2002).

Morgan et al., "Mechanical Properties of Carbonated Apatite Bone Mineral Substitute: Strength, Fracture and Fatigue Behavior," *J. Mater. Sci. Mater. Med.*, 8 559-570 (1997).

Nakahira et al., "Novel Synthesis Method of Hydroxyapatite Whiskers by Hydrolysis of $\alpha$-Tricalcium Phosphate in Mixtures of Water and Organic Solvent," *J. Am. Ceram. Soc.*, vol. 82 No. 8, 2029-2032 (1999).

Peter et al., "In Vivo Degradation of a Ploy(propylene fumarate)/$\beta$-tricalcium Phosphate Injectable Composite Scaffold," *J. Biomed. Mater. Res.*, 41 [1] 1-7 (1998).

Rho et al., "Mechanical Properties and the Hierarchical Structure of Bone," *Med. Eng. Phys.*, 20, 92-102 (1998).

Roeder et al., "Hydroxyapatite Whisker Reinforcements Used to Produce Anisotropic Biomaterials," *Trans. of the 47th Annual Meeting of the Orthopaedic Research Society*, San Francisco, CA 26 203 (2001).

Roeder et al., "Hydroxyapatite Whisker Reinforced PMMA and bis-GMA/TEG-ODMA Injectable Bone Cements," *Society for Biomaterials 27th Annual Meeting Trans.*, Minneapolis, MN, 24 203 (2001).

Roeder et al., "Hydroxyapatite Whiskers Provide Enhanced, Bone-Like Mechanical Properties in Reinforced Polymer Composites," *T4rans. of the 48th Annual Meeting of the Orthopaedic Research Society*, Dallas, TX, 27 1073 (2002).

Roeder et al., "Hydroxyapatite Whiskers Provide Impoorved Mechanical Properties in Reinforced Polymer Composites," submitted to *J. Biomed. Mater. Res.* in Aug. 2002.

Saito et al., "Hydroxyapatite Composite Resin as a New Bioactive Bone Cement," pp. 475-480 in *Bioceramics*, vol. 6, Proceedings of the 6th International Symposium on Ceramics in Medicine (Philadelphia, PA, November). Edited by P. Ducheyne and D. Christiansen, Butterworth-Heinemann Ltd., Oxford, 1993.

Sasaki et al., "Orientation of Bone Mineral and Its Role in the Anisotropic Mechanical Properties of Bone—Transverse Anisotropy," *J. Biomechanics*, 22, [2]2 157-164 (1989).

Sasaki et al., "Orientation of Mineral in Bovine Bone and Anisotropic Mechanical Properties of Plexiform Bone," *J. Biomechanics*, 24 [1]-57-61 (1991).

Sasaki et al., "X-ray Pole Figure Analysis of Apatite Crystals and Collagen Molecules in Bone," *Calcif. Tissue Int.*, 60, 361-367 (1997).

Shikinami et al., "Bioresorbable Devices made of Forged Composites of Hydroxyapatite (HA) particles and Poly-L-lactide IPLLA): Part I. Basic Characteristics," *Biomaterials*, 20, 859-877 (1999).

Shinzato et al., "Bioactive Polymethyl Methacrylate-based Bone Cement: Comparison of Glass Beads, Apatite- and Wollastonite-containing Glass-ceramic, and Hydroxyapatite Fillers on Mechanical and Biological Properties," *J. Biomed. Mater. Res.*, 51 [2] 258-272 (2000).

Suchanek et al., "Biocompatible Whiskers with Controlled Morphology and Stoichiomeytry ," *J. Mater. Res.*, 10 [3] 521-529 1994.

Suchanek et al., "Preparation of Fibrous, Porous Hydroxyapatite Ceramics from Hydroxyapatite Whiskers," *J. Am. Ceram. Soc.*, vol. 81, No. 3, 765-67 (1998).

Suchanek et al., "Processing and Mechanical Properties of Hydroxyapatite Reinforced with Hydroxyapatite Whiskers," *Biomaterials*, vol. 17, No. 17, 1715-1723 (1996).

Takano et al., "Mineral Anisotropy in Mineralized Tissues is Similar Among Species and Mineral Growth Occurs Independently of Collagen Orientation in Rats: Results from Acoustic Velocity Measurements," *J. Bone Miner. Res.*, 11 [9] 1292-1301 (1996).

Tanner et al. "Clinical Applications of Hydroxyapatite Reinforced Materials," *Brit. Ceram. Trans.*, 93 [3] 104-107 (1994).

That et al., "Fatigue Characterization of a Hydroxyapatite-reinforced Polyethylene Composite I. Uniaxial Fatigue," *J. Biomed. Mater. Res.*, 51 [3] 453-460 (2000).

That et al., "Fatigue Characterization of a Hydroxyapatite-reinforced Polyethylene Composite. II. Bioaxial Fatigue," *J. Biomed. Mater. Res.*, 53 [3] 461-468 (2000).

Ural et al., "Poly(D,L-lactide/$\epsilon$-caprolactone)/hyrdroxyapatite Composites," *Biomaterials*, 21 2147-2154 (2000).

Van Buskirk et al., "Ultrasonic Measurement of Orthotropic Elastic Constants of Bovine Femoral Bone," *J. Biomech. Eng.*, 103 [5] 67-72 (1981).

Wang et al., "Chemically Coupled Hydroxyapatite-polyethylene Composites: Processing and Characterisation," *Mater. Lett.*,44 [6] 119-124 (2000).

Wang et al., "Hydroxyapatite-Polyethylene Composites for Bone Substitution: Effects of Ceramic Particle Size and Morphology," *Boimaterials*, 19 [24] 2357-2366 (1998).

Wang et al., "Processing, Characterisation, and Evaluation of Hydroxyapatite Reinforced Polyethylene Composites," *Brit. Ceram. Tans.*, 93 [3] 91-95 (1994).

Wang et al., "Production and Evaluation of Hydroxyapatite Reinforced Polysulfone for Tissue Replacement," *J. of Material Science: Materials in Medicne*, vol. 12, 821-826 (2001).

Xu et al., "Reinforcement of a Self-setting Calcium Phosphate Cement with Different Fibers," *J. Biomed. Mater. Res.*, 52 [1] 107-114 (2000).

Xu et al., "Strong and Macroporous Calcium Phosphate Cement: Effects of Porosity and Fiber Reinforcement on Mechanical Properties," *J. Biomed. Mater. Res.*, 57 [3] 457-466 (2001).

Xu et al., "Whisker-reinforced Bioactive Composites Containing Calcium Phosphate Cement Fillers: Effects of Filler Ration and Surface Treatments on Mechanical Properties," *J. Biomed. Mater. Res.*, 57 [2] 165-174 (2001).

Yang et al., "Additive Modification of the Polymerization and Properties of an Acrylic bone Cement," *Polym. Engl. Sci.* 38 [3] 530-533 (1998).

Yoshimura et al., "Hydrothermal Synthesis of Biocompatible Whiskers," *J. Mater. Sci.*, 29 3399-3402 (1994).

Zhang, et al. "Porous Poly(L-lactic acid)apatite Composites Created by Biomimetic Process," *J. Biomed Mater. Res.*, vol. 45, 285-293 (1999).

Bakar et al., "Thermal processing of hydroxyapatite reinforced polyetheretherkeone composites," *J. Mater. Proc. Technol.*, 89-90: 462-466 (1999).

Chen et al., "Poly(DL-lactic-*co*-glycolic acid) sponge hybridized with collagen microsponges and deposited apatite particulates," *J. Biomed. Mater. Res.*, 57 [1]: 8-14 (2001).

Deb et al.,"Hydroxyapatite-polyethylene composites: effect of grafting and surface treatment of hydroxyapatite," *J. Mater. Sci. Mater. Med.*, 7 [4]: 191-193 (1996).

Devin et al., "Three-dimensional degradable porous polymer-ceramic matrices for use in bone repair," *J. Biomater. Sci. Polymer Edn.*, 7 [8]: 661-669 (1996).

Domingo et al., "Dental composites reinforced with hydroxyapatite: Mechanical behavior and absorption/elution characteristics," *J. Biomed. Mater. Res.*, 56 [2]: 297-305 (2001).

Du et al., "Formation of calcium phosphate/collagen composites through mineralization of collagen matrix," *J. Biomed. Mater. Res.*, 50 [4]: 518-527 (2000).

Elgendy et al., "Osteoblast-like cell (MC3T3-E1) proliferation on bioerodible polymers: an approach towards the development of a bone-bioerodible polymer composite material," *Biomaterials*, 14 [4]: 263-269 (1993).

Endoh et al., "Shape estimation of anisometric particles using size measurement techniques," *Part. Part. Syst. Charact.*, 15: 145-149 (1998).

Frayssinet et al., "Osteointegration of composite calcium phosphate bioceramics," *J. Biomed. Mater. Res.*, 50 [2]: 125-130 (2000).

Furukawa et al., "Histomorphometric study on high-strength hydroxyapatite/poly(L-lactide) composite rods for internal fixation of bone fractures," *J. Biomed. Mater. Res.*, 50 [3]: 410-419 (2000).

Gauthier et al., "Kinetic Study of Bone Ingrowth and Ceramic Resorption Associated with the Implantation of Different Injectable Calcium-Phosphate Bone Substitutes," *J. Biomed. Mater. Res.*, 47: 28-35 (1999).

Kibbel et al., "Anisometric shape factors for ceramic microstructures," *J. Am. Ceram. Soc.*, 73[3]: 517-519 (1989).

Li et al., "A novel injectable bioactive bone cement for spinal surgery: a developmental and preclinical study," *J. Biomed. Mater. Res.*, 52 [1]: 164-170 (2000).

Linhart et al., "Biologically and chemically optimized composites of carbonated apatite and polyglycolide as bone substitution materials," *J. Biomed. Mater. Res.*, 54 [2]: 162-171 (2000).

Liu et al., "Nano-apatite/polymer composites: mechanical and physicochemical characteristics," *Biomaterials* 18 [19]: 1263-1270 (1997).

Ma et al., "Engineering new bone tissue in vitro on highly porous poly($\alpha$-hydroxy acids)/hydroxyapatite composite scaffolds," *J. Biomed. Mater. Res.*, 54 [2]: 284-283 (2000).

Meenan et al., "Thermal analysis studies of poly(etheretherketone)/hydroxyapatite biocomposite mixtures," *J. Mater. Sci. Mater. Med.*, 11: 481-489 (2000).

Okada et al., "Ultrastructure of the interface between bioactive composite and bone: Comparison of apatite and wollastonite containing glass-ceramic filler with hydroxyapatite and $\beta$-tricalcium phosphate fillers," *J. Biomed. Mater. Res.*, 57 [1]: 101-107 (2001).

Rhee et al. "Synthesis of Hydroxyapatite/Collagen/Chondroitin Sulfate Nanocomposite by a Novel Precipitation Method," *J. Am. Ceram. Soc.*, 84 [2]: 459-461 (2001).

Rizzi et al., "Biodegradable polymer/hydroxyapatite composites: Surface analysis and initial attachment of human osteoblasts," *J. Biomed. Mater. Res.*, 55 [4]: 475-486 (2001).

Sasaki et al., "Mechanical properties of hydroxyapatite-reinforced gelatin as a model system of bone," *Biomaterials*, 10: 129-132 (1989).

Serre et al., "In vitro induction of a calcifying matrix by biomaterials constituted of collagen and/or hydroxyapatite: an ultrastructural comparison of three types of biomaterials," *Biomaterials*, 14 [2]: 97-106 (1993).

Silvio et al., "Osteoblast behaviour on HAP/PE composite surfaces with different HA volumes," *Biomaterials*, 23: 101-107 (2002).

Sim et al "Injection moulding of hydroxyapatite composites," *J. Mater. Proc. Technol.*, 69: 75-78 (1997).

Tenhuisen et al., "The formation of hydroxyapatite-gelatin composites at 38° C.," *J. Biomed. Mater. Res.*, 28: 27-33 (1994).

Utracki, "Flow and flow orientation of composites containing anisometric particles," *Polymer Composites*, 7 [5]: 274-282 (Oct. 1986).

Verheyen et al., "Evaluation of hydroxylapatite/poly(L-lactide) composites: physico-chemical properties," *J. Mater. Sci. Mater. Med.*, 4: 58-65 (1993).

Verheyen et al., "Hydroxylapatite/poly(L-lactide) composites: An animal study on push-out strengths and interface histology," *J. Biomed. Mater. Res.*, 27: 433-444 (1993).

Verheyen et al., "Evaluation of hydroxylapatite/poly(L-lactide) composites: Mechanical behavior," *J. Biomed. Mater. Res.*, 26: 1277-1296 (1992).

Watson et al., "The formation of hydroxyapatite-calcium polyacrylate composites," *J. Mater. Sci. Mater. Med.*, 10: 205-213 (1999).

Yamaguchi et al., "Preparation and microstructure analysis of chitosan/hydroxyapatite nanocomposites," *J. Biomed. Mater. Res.*, 55 [1]: 20-27 (2001).

Zhang et al., "Poly($\alpha$-hydroxyl acids)/hydroxyapatite porous composites for bone tissue engineering. I. Preparation and morphology," *J. Biomed. Mater. Res.*, 44: 446-455 (1999).

Weiler et al., "Enhancement of the Mechanical Properties of Polylactides by Solid-state Extrusion," *Biomaterials*, 17: 529-535 (1996).

Zachariades et al., "Recent Developments in Ultraorientation of Polyethylene by Solid State Extrusion," *Chem. Rev.*, 80: 351-364 (1980).

Bakar et al., "Mechanical Properties of Injection Molded Hydroxyapatite-polyetheretherketone Biocomposites," *Compos. Sci. Technol.*, 63: 421-425 (2003).

Converse et al., "Processing and Tensile Properties of Hydroxyapatite-whisker-reinforced Polyetheretherketone," *Biomaterials*, 28: 927-935 (2007).

Roeder et al., "Hydroxyapatite Whiskers Provide Improved Mechanical Properties in Reinforced Polymer Composites," *J. Biomed. Mater. Res.*, 67A: 801-812 (2003).

* cited by examiner

COMPOSITE BIOMATERIAL INCLUDING ANISOMETRIC CALCIUM PHOSPHATE REINFORCEMENT PARTICLES AND RELATED METHODS

CROSS-REFERENCE TO RELATED APPLICATIONS

The present application claims the benefit of U.S. application No. 60/179,238, filed on Jan. 31, 2000, which is hereby incorporated in its entirety by reference.

TECHNICAL FIELD OF THE INVENTION

This invention pertains generally to biomaterials. More particularly, the present invention relates to a composite biomaterial that can be used, for example, as an orthopedic implant.

BACKGROUND OF THE INVENTION

Orthopedic implants are used commonly as structural reinforcements in the human body. By way of example, orthopedic implants are used to strengthen failed bone (e.g., broken or deteriorating bone), to stiffen compromised vertebrae, or to eliminate painful arthritic or damaged joints. Most orthopedic implants presently in use involve the extensive use of permanent metal hardware, such as, for example, bone plates and screws and spine cages.

Despite the enhanced mechanical strength and stiffness associated with them, such traditional metallic orthopedic implants require invasive surgical techniques which impose a large degree of surgical trauma, suffering, and rehabilitation time on patients. As an example, the treatment of hip fractures often requires an incision that is twelve inches or longer. Furthermore, when a stiff metal plate or implant is attached to bone, it tends to "shield" the bone tissue from mechanical stresses, and, under these conditions, native bone undesirably tends to resorb away.

Nevertheless, finding suitable alternative biomaterials has proven to be difficult. Particularly, existing non-metal biomaterials have not been satisfactory, for example, because they are inadequate with respect to mechanical properties (e.g., strength). For example, dense ceramics would have similar problems because they are stiff, and, thus, are stress shielding, and they have the additional drawback of being brittle such that they have a lower fracture toughness. In addition, non-metal biomaterials, such as, for example, existing polymeric and porous ceramic biomaterials are significantly inferior to natural cortical bone in terms of mechanical properties, such as, for example, elastic modulus, tensile strength, and compressive strength.

By way of example, one alternative approach to the use of metals in the field of orthopedics involves minimally invasive orthopedic implant surgical techniques in which injectable bone glue and filler materials are used (e.g., to repair a bone fracture) instead of metal plates and screws and the like. As an example, the "skeletal replacement system" (SRS) offered by Norian Corporation (Cupertino Calif.) involves an injectable cementitious material that cures after injection in the body (i.e., in vivo). However, the SRS material has proven to be unsatisfactory for many load bearing applications because of its inferior tensile properties and low fracture toughness.

In addition, noteworthy among polymeric materials is the polymethyl methacrylate (PMMA) cement. The PMMA cement also suffers from insufficient mechanical properties, which, while generally better than SRS, are still inferior to those of natural cortical bone. In addition, another shortcoming associated with PMMA cement is that a large amount of heat is generated undesirably during the exothermic curing process. The heat generated during the exothermic curing reaction limits the volume of a bone defect that can be filled inasmuch as a large volume of bone cement will generate sufficient heat to kill adjacent tissues. Furthermore, PMMA cement also has a tendency to leach out MMA monomer that can have toxic effects on nearby tissues.

Accordingly, it will be appreciated from the foregoing that there exists a need in the art for a biomaterial (e.g., for orthopedic implants) with desirable biomechanical properties, as well as methods of preparing such biomaterials. It is an object of the present invention to provide such a biomaterial and related methods. These and other objects and advantages of the present invention, as well as additional inventive features, will be apparent from the description of the invention provided herein.

BRIEF SUMMARY OF THE INVENTION

The present invention provides a composite biomaterial as well as methods of preparing composite biomaterials. The composite biomaterial includes anisometric calcium phosphate reinforcement particles that are dispersed within a matrix. The matrix comprises a thermoplastic polymer, a calcium phosphate composition that is curable in vivo (e.g., in a mammal), or any combination thereof.

In another aspect of the present invention, provided is a method of preparing a composite biomaterial comprising (a) a matrix including a calcium phosphate composition that is curable in vivo and (b) anisometric calcium phosphate reinforcement particles arranged within the matrix. The method comprises providing the anisometric calcium phosphate reinforcement particles. The method also includes preparing the calcium phosphate composition from at least one calcium-containing compound and at least one phosphate-containing compound. At least one of the calcium-containing compound and phosphate-containing compound is derived by a hydrothermal reaction. In addition, the method comprises combining the anisometric calcium phosphate reinforcement particles with the calcium phosphate composition or, alternatively, with at least one of the calcium-containing compound or phosphate-containing compound prior to formation of the calcium phosphate composition.

In addition, in another aspect, the present invention provides a method of preparing a composite biomaterial comprising (a) a matrix including a thermoplastic polymer and (b) anisometric calcium phosphate reinforcement particles arranged within the matrix. The method comprises providing the anisometric calcium phosphate reinforcement particles and providing the polymer. The method also includes co-processing the polymer and the calcium phosphate reinforcement particles to obtain a substantially uniform mixture thereof. In addition, the method comprises deforming and/or densifying the mixture to form the composite biomaterial.

The invention may best be understood with reference to the accompanying drawings and the following detailed description of the preferred embodiments.

DETAILED DESCRIPTION OF THE INVENTION

The present invention is predicated, at least in part, on providing composite biomaterials that are biocompatible and have desirable biomechanical properties (e.g., resembling those of natural bone). The biomaterials include a matrix (e.g., continuous phase or continuum) of, for example, a thermoplastic polymer, a calcium phosphate composition, or suitable combinations thereof. Significantly, the composite biomaterials of the present invention also include calcium phosphate reinforcement particles, which are dispersed within the matrix, in order to provide mechanical reinforcement. In accordance with the present invention, the calcium phosphate reinforcement particles are either single crystals or dense polycrystals and are anisometric (as opposed to equiaxed) in nature such that the reinforcement particles exhibit different properties in different orientations or crystallographic directions. As a result of the anisometric nature of the reinforcement particles, especially if aligned (as discussed herein below), the inventive composite biomaterials possess enhanced biomechanical properties. The composite biomaterials of the present invention have significant utility, for example, in mammalian orthopedic implants (e.g., as a prosthesis for replacement of bone).

The matrix can be bioresorbable (i.e., a material capable of being resorbed by a patient, e.g., a mammal, under normal physiological conditions) or non-bioresorbable, as desired. In this respect, in some applications, it is desirable that the biomaterial be bioresorbable by the patient, such as, for example, in younger patients where bone regeneration occurs readily. Desirably, in some embodiments, bioresorbable materials are selected so as to be tailored to the particular patient's own bone regeneration process such that the bioresorbable material would be replaced gradually over time by the patient's own natural (regenerated) tissue.

In other applications, non-bioresorbability is desirable, e.g., in older patients where bone regeneration is retarded, so that the biomaterial remains inert and demonstrates little degradation in biomechanical properties. However, the decision of whether to use a bioresorbable or non-bioresorbable biomaterial depends on many factors including the patient's health profile, the degree of injury, and the procedure preferred by the surgeon.

The biomaterial can be percutaneously injected, surgically injected, or surgically implanted, depending upon the material or materials selected for the matrix. By way of example, in embodiments where a major portion of the matrix is a calcium phosphate composition or a thermoplastic polymer composition that exhibits flowability initially but is capable of curing (setting up) in vivo in a mammalian host after some period of time, percutaneous or surgical injection (e.g., via a needle, catheter, glue gun or the like) can be utilized to deliver the inventive biomaterial while in the flowable state to the desired in vivo location. In other embodiments, the initially flowable composition can be cured and formed into a desired shape ex vivo and surgically implanted. In still other embodiments, for example, where a major portion of the matrix includes a calcium phosphate composition or a thermoplastic polymer composition where in vivo delivery by injection and/or curing is not possible or sufficiently limited, the biomaterial can be appropriately shaped by the surgeon and surgically implanted.

Any suitable calcium phosphate composition (e.g., cement) or thermoplastic material, as well as suitable combinations thereof, can be included in the matrix. By way of example, and not limitation, examples of suitable calcium phosphate compounds for inclusion (alone or in combination) in the calcium phosphate composition are listed in Table I. In addition, one or more dopants (e.g., sodium, potassium, magnesium, carbonate, fluoride, chloride, and the like) optionally can be included in the calcium phosphate composition. If included, the dopants preferably are included in an amount of less than about 10% by weight of the calcium phosphate composition.

TABLE I

Exemplary Calcium Phosphate Compounds

| Abbrev. | Chemical Formula | Chemical Name | Mineral Name |
|---|---|---|---|
| ACP | $Ca_x(PO_4)_y$ | Amorphous calcium phosphate | |
| BCP | $(Ca_{10}(PO_4)_6OH)_x +$ $(Ca_3(PO_4)_6)_{1-x}$ | biphasic calcium phosphate | |
| CP | | calcium phosphate | |
| DCP | $CaHPO_4$ | dicalcium phosphate | Monetite |
| DCPD | $CaHPO_4 \cdot 2H_2O$ | dicalcium phosphate dihydrate | Brushite |
| HA or OHAp | $Ca_{10}(PO_4)_6(OH)_2$ | calcium hydroxyapatite | Apatite or hydroxyapatite |
| $CO_3Ap$ | $Ca_{10}(PO_4)_6(OH)_2$ with $CO_3$'s substituting $PO_4$'s and/or OH's | carbonated calcium hydroxyapatite | Carbonate apatite |
| MCP | $Ca(H_2PO_4)_2$ | monocalcium phosphate | |
| MCPM | $Ca(H_2PO_4)_2 \cdot H_2O$ | monocalcium phosphate monohydrate | |
| OCP | $Ca_8H_2(PO_4)_6 \cdot 5H_2O$ | octacalcium phosphate | |
| TCP | $Ca_3(PO_4)_2$ | tricalcium phosphate | |
| α-TCP | $\alpha\text{-}Ca_3(PO_4)_2$ | alpha-tricalcium phosphate | |
| β-TCP | $\beta\text{-}Ca_3(PO_4)_2$ | beta-tricalcium phosphate | |
| TTCP | $Ca_4(PO_4)_2O$ | Tetra-calcium phosphate | Hilgenstockite |

As will be appreciated by one skilled in the art, the bioresorbability of these calcium phosphate compounds varies according to crystal chemistry.

Referring now to thermoplastic polymers, examples of bioresorbable thermoplastics include, but are not limited to, poly(DL-lactide) (DLPLA), poly(L-lactide) (LPLA), poly(g- lycolide) (PGA), poly(ε-caprolactone) (PCL), poly(dioxanone) (PDO), poly(glyconate), poly(hydroxybutyrate) (PHB), poly(hydroxyvalerate (PHV), poly(orthoesters), poly (carboxylates), poly(propylene fumarate), poly(phosphates), poly(carbonates), poly(anhydrides), poly(iminocarbonates), poly(phosphazenes), and the like, as well as copolymers or blends thereof, and combinations thereof.

Examples of non-bioresorbable thermoplastics include, but are not limited to, polyethylenes, such as high density polyethylene (HDPE), ultra high molecular weight polyethylene (UHMWPE), and low density polyethylene (LDPE), as well as polybutylene, polystyrene, polyurethane, polypropylene, polyacrylates, polymethacrylates, such as polymethylmethacrylate (PMMA), and polymerized monomers such as tri(ethylene glycol) dimethacrylate (TEG-DMA), bisphenol a hydroxypropyl methacrylate (bis-GMA), and other monomers listed herein below, and the like, as well as copolymers or blends thereof and combinations thereof.

In some embodiments, the matrix can include a combination of calcium phosphate compounds, a combination of thermoplastics, or a combination of one or more calcium phosphate compounds and one or more thermoplastics. Strictly by way of example, in some embodiments, the matrix can include a combination of at least one non-bioresorbable material (e.g., thermoplastic or calcium phosphate) and at least one bioresorbable material. For example, the matrix can include at least one calcium phosphate compound as well as particulate or dissolved (e.g., in water or other suitable biocompatible medium) thermoplastic.

Desirably, in some embodiments in which the matrix includes a combination of a non-bioresorbable material and a bioresorbable material, the matrix can be arranged so that the concentration of the bioresorbable component is higher at or near the matrix surface. In this respect, the bioresorbable component can be graded from the matrix surface to the inner core of the matrix.

Figure 1:
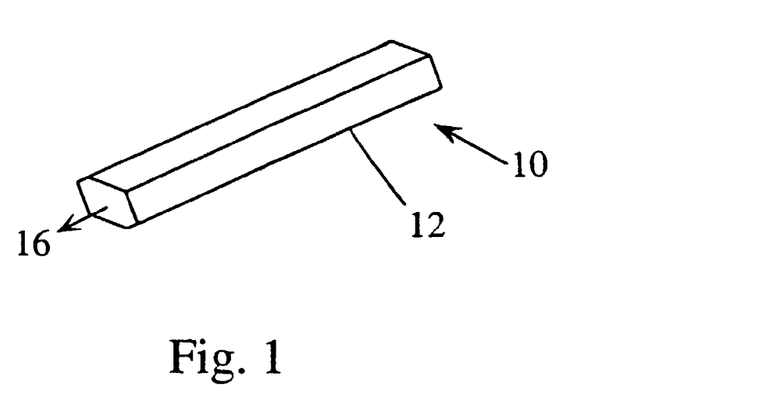
FIG. 1 is a schematic representation of a whisker-shaped anisometric reinforcement particle, in accordance with the present invention.
Figure 2:
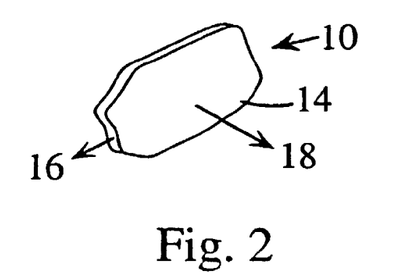
FIG. 2 is a schematic representation of a platelet-shaped anisometric reinforcement particle, in accordance with the present invention.

With respect to the reinforcement particles, the particular calcium phosphate utilized for the reinforcement particles can be selected, for example, from the list in Table I, as well as combinations thereof. Dopants or other additives can be included within the reinforcement particles, if desired. In accordance with the present invention, the calcium phosphate reinforcement particles are in the form of single crystals or dense polycrystals, and are anisometric in nature. For example, the calcium phosphate reinforcement particles 10 can be in the shape of whiskers 12, as shown in FIG. 1, or in the shape of platelets 14, as shown in FIG. 2. In particular, the reinforcement particles are characterized as having a c-axis 16, which is the longest othogonal axis, and an a-axis 18, which is the shortest othogonal axis, as shown in FIGS. 1 and 2. Pursuant to the present invention, inasmuch as the reinforcement particles are anisometric (and not equiaxed), the respective lengths along the c-axis and the a-axis are different. In this respect, the reinforcement particles of the present invention are characterized as having a mean aspect ratio (length along c-axis/length along a-axis) of greater than 1 and less than 100. Preferably, the mean aspect ratio of the reinforcement particles is from about 5 to about 50, more preferably, from about 7.5 to about 35, and still more preferably, from about 10 to about 20.

The reinforcement particles can be of any suitable size. For example, in some embodiments, the reinforcement particles have mean dimensions of from about 1 micrometer to about 500 micrometers along the c-axis and from about 0.02 micrometers to about 20 micrometers along the a-axis. Other exemplary mean dimensions include a length of from about 5 micrometers to about 50 micrometers along the c-axis and a length of from about 0.1 micrometer to about 10 micrometers along the a-axis. Additional exemplary mean dimensions include a length of from about 10 micrometers to about 40 micrometers along the c-axis and a length of from about 0.2 micrometers to about 8 micrometers along the a-axis.

In addition, some smaller, (e.g., nano-sized) calcium phosphate reinforcement particles can be included as well. For example, the nano-sized (e.g., mean dimensions of from about 1 nanometers to about 500 nanometers) can be in the form of bioresorbable particles, in which case the smaller size would be advantageous because resorption would occur more readily. Desirably, if present, the nano-sized reinforcement particles are concentrated more heavily at or near the matrix surface. In particular, if present, the nano-sized calcium phosphate reinforcement particles preferably are graded from the matrix surface to the inner core of the matrix.

The reinforcement particles can be included in any suitable amount in the inventive composite biomaterial. For example, the reinforcement particles can be provided in an amount of from about 1% by volume of the composite biomaterial to about 60% by volume of the composite biomaterial, more preferably, from about 30% by volume of the composite to about 60% by volume of the composite, still more preferably, from about 40% by volume of the composite to about 60% by volume of the composite.

Figure 3:
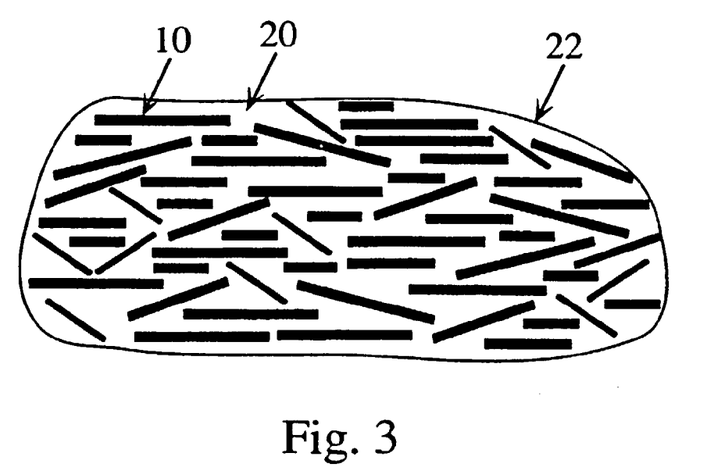
FIG. 3 is a schematic representation of a cross-section of a composite biomaterial, illustrating anisometric reinforcement particles dispersed in a matrix in an aligned manner, in accordance with a preferred embodiment of the present invention.

Notably, the calcium phosphate reinforcement particles provide mechanical reinforcement (e.g., strength and/or fracture toughness), for example, because of their anisometric morphology and because of their nature as single-crystals or dense polycrystals which have greater inherent mechanical properties as compared to the matrix. With respect to morphology, because the reinforcement particles geometrically are anisometric, the particles effectively reinforce the biomaterial. Particularly, the anisometric reinforcement particles 10 can be provided so that they are dispersed in the matrix 20, preferably so that there is overlap between particles, as seen in FIG. 3, so that reinforcement is enhanced. For purposes of clarity, the term "dispersed" does not preclude some contact between particles.

The reinforcement particles can be randomly oriented (i.e., unaligned) in some embodiments. However, as seen in FIG. 3, the reinforcement particles 10 preferably are predominately aligned within the matrix 20. Crystallographic or morphological alignment (e.g., a preferred orientation) of the reinforcement particles within the matrix 20 results in anisotropy for the overall composite 22. By way of contrast, if the reinforcement particles are randomly oriented (i.e., no preferred orientation) within the matrix, the overall composite possesses isotropic properties. Composites exhibiting anisotropic properties, that is, having different properties in different directions of the composite, possess enhanced mechanical properties in one or two directions of the composite over composites exhibiting isotropic properties, that is, having equal properties in all directions, all else being equal. In many cases (for example, the long shaft of the femur), the unique mechanical properties possessed by native human bone are due to anisotropy.

As used herein, the term "aligned" reinforcements will be understood by those of ordinary skill in the art as a preferred crystallographic or morphological orientation. The preferred orientation or texture of a material is most accurately measured quantitatively by way of an orientation distribution function (ODF). An ODF can be measured using x-ray diffraction pole figure analysis and/or stereological analysis, as described by Sandlin et al., "Texture Measurement on Materials Containing Platelets Using Stereology," *J. Am. Ceram. Soc.*, 77 [8] 2127-2131 (1994). In these quantitative techniques, a random ODF is assigned a value of 1, such that values greater than 1 indicate a preferred (aligned) orientation in multiples of a random distribution (MRD). In accordance with preferred embodiments of the invention, the reinforcement particles are aligned in the matrix such that they have an ODF pursuant to this quantitative technique of greater than 1 MRD, more preferably, an ODF of at least about 2 MRD, even more preferably an ODF of at least about 3 MRD, still more preferably, an ODF of at least about 4 MRD, even more preferably an ODF of at least about 5 MRD, e.g., an ODF of from about 5-20 MRD, which approximately corresponds to that of the human femur. In some embodiments, it is desirable to have an even higher ODF, for example, an ODF of at least about 20, to achieve mechanical anisotropy in the synthetic composite biomaterial that matches the host's bone material As will be appreciated by those of ordinary skill in the art, semi-quantitative techniques of identifying the preferred (aligned) orientation or texture of a material are described by Harris (see, e.g., "Quantitative Measurement of Preferred Orientation in Rolled Uranium Bars," *Phil. Mag.* 43 [336] 113-123 (1952); and Peterson et al., "X-Ray Texture Analysis of Oriented PZT Thin Films," *Mat. Res. Joc. Symp. Proc.,* 433, 297-302 (1996)) and Lotgering (see, e.g., "Topotactical Reactions with Ferrimagnetic Oxides Having Hexagonal Crystal Structures—I," *J. Inorg. Nucl. Chem.,* 9, 113-123 (1959)). It will be appreciated that under the Harris technique, a random orientation also is assigned a value of 1, while in the Lotgering technique, the random orientation is assigned a value of zero. Thus, a preferred, or aligned, orientation would have a volume greater than 1 or zero, respectively, under these semi-quantitative techniques.

In addition to their morphology, the inherent strength of the reinforcement particles, which is greater than that of the matrix, enhances the mechanical strength of the composite. In this respect, whereas the matrix can include a porous material of polycrystals (e.g., cement), the reinforcement particles are not porous and are unitary crystals. The porosity of the matrix is biologically advantageous but undesirable with respect to mechanical strength. Accordingly, the reinforcement particles enhance the mechanical strength of the composite biomaterial of the present invention.

The inventive composite biomaterial optionally can include additives, if desired. By way of example, the biomaterial can include one or more surface-active agents in order to enhance interfacial bonding between the reinforcement particles and the matrix. As other examples, the inventive biomaterial can include one or more growth factors, including, but not limited to, those in the TGF-beta super family (e.g., TGF-betas, bone morphogenic proteins, such as, for example, BMP-2, BMP-7 or the like, etc.), fibroblast growth factors, epidermal growth factors, vascular endothelial growth factors, insulin-like growth factors, or interleukins, to enhance osteoinductivity and/or bone regeneration. Furthermore, the inventive biomaterial can include one or more transcription factors or matrix metalloproteinases to improve bone regeneration, or speed resorption and replacement of the biomaterial. In addition, the biomaterial can be coated with one or more peptides or proteins that enhance attachment of bone cells (e.g., osteopontin, integrins, matrix receptors, RGD, or the like).

The anisometric calcium phosphate particles can be prepared in any suitable manner. Suitable techniques are described, for example, in U.S. Pat. No. 5,227,147; Fujishiro et al., "Preparation of Needle-like Hydroxyapatite by Homogeneous Precipitation under Hydrothermal Conditions," *J. Chem. Technol. Biotechnol.,* 57, 349-353 (1993); Yoshimura et al. "Hydrothermal Synthesis of Biocompatible Whiskers," *J. Mater. Sci.,* 29, 3399-3402 (1994); Suchanek et al., "Biocompatible Whiskers with Controlled Morphology and Stoichiometry," *J. Mater. Res.,* 10 [3] 521-529 (1995); Kandori et al., "Texture and Formation Mechanism of Fibrous Calcium Hydroxyapatite Particles Prepared by Decomposition of Calcium-EDTA Chelates," *J. Am. Ceram. Soc.,* 80 [5] 1157-1164 (1997); Nakahira et al., "Novel Synthesis Method of Hydroxyapatite Whiskers by Hydrolysis of α-Tricalcium Phosphate in Mixtures of Water and Organic Solvent," *J. Am. Ceram. Soc.,* 82 [8] 2029-2032 (1999); and Katsuki et al., "Microwave-Versus Conventional-Hydrothermal Synthesis of Hydroxyapatite Crystals from Gypsum," *J. Am. Ceram. Soc.,* 82 [8] 2257-2259 (1999).

In some embodiments, the reinforcement particles can be produced by way of a hydrothermal reaction, e.g., at low temperatures (such as, for example, from about 37° C. to about 200° C.) from chemical solutions containing chemical reactant precursors, pH modifying precursors, and/or chelating acids. In particular, the reactant precursors can be in the form of a calcium-containing compound and a phosphate-containing compound, both of which are selected such that they exhibit greater solubility in water than the solubility in water of the calcium-containing reinforcement particles desired to be produced (e.g., via precipitation or ion exchange in solution). Examples of such calcium-containing compounds include, but are not limited to, the compounds listed in Table I, as well as calcium hydroxide, calcium nitrate, calcium chloride, calcium carbonate, calcium lactate, calcium acetate, calcium citrate, calcium sulfate, calcium fluoride, calcium oxalate, and the like, as well as combinations thereof. Examples of phosphate-containing compounds include, but are not limited to, the compounds listed in Table I, as well as phosphoric acid, fluorophosphoric acid, sodium orthophosphate, potassium orthophosphate, ammonium orthophosphate, and the like, as well as combinations thereof. It will be appreciated that pH modifying precursors can include any suitable acid or base. Chelating acids can include, for example, formic acid, acetic acid, lactic acid, valeric acid, ethylenediaminetetracetic acid (EDTA), glycolic acid, oxalic acid, citric acid, and the like, as well as combinations thereof.

Producing the reinforcement particles hydrothermally is desirable because the size and morphology of the resulting reinforcement particles can be controlled readily, for example, by adjusting the reactant concentrations solution pH, type of chelating acid, reaction heating rate, mixing reaction temperature, and length of reaction. Reaction temperatures, for example, greater than 100° C., are especially conducive to whisker formation. It is to be noted, however, that reactions at temperatures greater than 100° C. require a pressure vessel that is suitably lined (e.g., with TEFLON®) to contain the pressurized aqueous solution.

Turning now to the preparation of the composite biomaterials, a matrix including at least one calcium phosphate composition (that is curable in vivo) can be prepared from one or more calcium-containing and one or more phosphate-containing reactant compounds. Notably, at least one of the calcium-containing or phosphate-containing reactant compounds is derived by a hydrothermal reaction. In some embodiments, both the calcium-containing and phosphate-containing reactant compounds are derived hydrothermally.

Particularly, by utilizing a hydrothermal reaction to derive at least one of the calcium-containing and phosphate-containing reactant compounds, the resultant reactant compounds can be produced so as to have a very fine size and controlled purity. Preferably, at least one of the calcium-containing and phosphate-containing reactant compounds is characterized by particles having a mean diameter of less than about 1 micrometer, more preferably, a mean diameter of from about 1 nanometer to about 500 nanometers, even more preferably, from about 1 nanometer to about 100 nanometers. By starting with a smaller grain size for one or both of the calcium-containing and phosphate containing reactant compounds, the resulting calcium phosphate matrix composition also would be in the form of smaller particles (e.g. polycrystals). The smaller size of the particles of the calcium phosphate matrix composition results in a matrix of enhanced mechanical strength.

The calcium-containing and phosphate-containing reactant compounds can be selected, for example, from the respective lists of calcium-containing and phosphate-containing chemical precursors discussed herein above with respect to the reinforcement particles. To produce the calcium phosphate matrix composition, the calcium-containing and phosphate-containing reactant compounds can be mixed, for example, while dry (e.g., in powder form). In some embodiments, the powders can be mixed with phosphoric acid crystals and ground with mortar and pestle. In addition, as an example, a sodium phosphate solution can be added to form a flowable paste, which is injectable into a patient and which is capable of curing in vivo in a mammalian host after injection at the desired locus (e.g., bone, such as the femur or vertebrae). In this respect, the paste desirably is formed, for example, in the operating room, shortly before delivery (e.g., by injection) into the patient where it can then harden in vivo. In other embodiments, the compounds can be prepared in two separate flowable pastes which can be stored separately, and later mixed together and injected at the desired locus where it can harden in vivo.

The calcium phosphate reinforcement particles can be added prior to formation of the calcium phosphate composition (e.g., added to one or both of the calcium-containing compound(s) and phosphate-containing compound(s)) and/or after the calcium phosphate composition is formed.

With respect to the preparation of a composite biomaterial comprising a matrix that includes at least one thermoplastic polymer, a substantially uniform mixture of polymer and calcium phosphate reinforcement particles is formed via co-processing. By way of example, in some embodiments, a preform is made from polymer provided in the form of particles. The polymer particles can be produced in any suitable manner. For example, the polymer can be dissolved in any suitable solvent in which the polymer can be dissolved (e.g., water, xylene, chloroform, toluene, methylene chloride, tetrahydrofuran, ethyl acetate, hexafluoroisopropanol, acetone, alcohols, and the like). In such embodiments, the polymer particles can be formed by precipitation or gelation from the solution, for example, under rapid mixing. The solvent is then removed, e.g., by vacuum oven drying, distillation and collection, freeze drying, and the like. Additionally, the polymer particles and/or gel may be suspended in a suitable medium (e.g., water, alcohols, and the like) and homogenized by high shear mixing to provide a uniform distribution of particles or repeatedly washed to remove residual traces of the solvent. The polymer particles and the calcium phosphate reinforcement particles each are suspended in a suitable medium for dispersing the particles, (e.g., water, alcohols, and the like). The preform is then formed by wet co-consolidation of the polymer and calcium phosphate particulate suspension.

In other embodiments, a preform is formed from a polymer foam, e.g., having open porosity (e.g., continuous). The polymer foam can be provided in a similar manner to the preparation of the polymer particles, but while dissolving the polymer at a slower mixing rate, with slower solvent removal, and at a higher fraction of polymer relative to solvent. Thus, the polymer foam is formed by dissolving the polymer in solvent (e.g., water, xylene, chloroform, toluene, methylene chloride, tetrahydrofuran, ethyl acetate, hexafluoroisopropanol, acetone, alcohols, and the like) while mixing followed by precipitation or gelation from the solution, followed by solvent removal via vacuum oven drying, distillation and collection, freeze drying, and the like. Additionally, the polymer foam and/or gel may be suspended in a suitable medium (e.g., water, alcohols, and the like) and repeatedly washed to remove residual traces of the solvent. In these embodiments, the co-processing includes infiltrating the polymer foam with a suspension (e.g., alcohols, in water and the like) of the calcium phosphate particles, so as to form the preform.

In still other embodiments, a preform is formed from a porous compact of the calcium phosphate reinforcement particles. The thermoplastic polymer is provided and infiltrated into the porous calcium phosphate compact. By way of example, the polymer can be provided molten, solvated (e.g., in a biocompatible medium, such as water or other medium that dissolves the thermoplastic), or as a polymerizing mixture comprising monomer, initiator, and, optionally, polymer powder and/or co-initiators (as discussed herein below). By way of example, the porous compact of the calcium phosphate reinforcement particles is produced, for example, by dry pressing the calcium phosphate particles and sintering (e.g., at temperatures of from about 600° C. to about 1000° C.) the dry pressed particles to form the compact. In the co-processing, the porous compact of the calcium phosphate reinforcement particles is infiltrated with the polymer.

Once the preform is formed, it is thermo-mechanically densified and deformed to form the composite biomaterial. By way of example, the preform can be thermo-mechanically densified and deformed via channel die forging, injection molding, extrusion, pultrusion, or the like. In addition, the thermo-mechanical deformation and densification desirably can include aligning the calcium phosphate reinforcement particles morphologically and/or crystallographically. The composite can be delivered to the patient, for example, by way of surgical implantation.

In still further embodiments, where a major portion of the matrix is a thermoplastic polymer composition and the composite biomaterial is to be delivered by either percutaneous or surgical injection, the thermoplastic polymer matrix may also be provided by mixing combinations of polymer powders and monomers with the addition of initiators and co-initiators (e.g., benzoyl peroxide, dimethylaniline, ascorbic acid, cumene hydroperoxide, tributylborane, sulfinic acid, 4-cyanovaleric acid, potassium persulfate, dimethoxybenzoine, benzoic-acid-phenylester, N,N-dimethyl p-toluidine, dihydroxy-ethyl-p-toluidine, and the like, and combinations thereof) to induce polymerization and hardening in-situ during composite co-processing. Exemplary monomers include, but are not limited to, acrylic monomers such as, for example, methylmethacrylate (MMA), 2,2'-bis(methacryloylethoxyphenyl) propane (bis-MEEP), bisphenol a polyethylene glycol diether dimethacrylate (bis-EMA), urethane dimethacrylate (UDMA), diphenyloxymethacrylate (DPMA), n-butylmethacrylate, tri(ethylene glycol) dimethacrylate (TEG-DMA), bisphenol a hydroxypropylmethacrylate (bis-GMA), and the like, and combinations thereof. Additionally, stabilizers (e.g., hydroquinone, 2-hydroxy-4-methoxy-benzophenone, and the like, and combinations thereof) may be added to mixtures to prevent premature polymerization of the monomers. The calcium phosphate reinforcements may be provided and mixed into any part of the polymer mixture prior to, during or after the polymer mixture is formed, yielding a flowable, polymerizing composite biomaterial. Additionally, the polymer and or composite mixture may be mixed under vacuum or centrifuged to minimize porosity caused by entrapped gases. The polymer mixture is viscous in nature and gradually hardens (or "cures") as polymerization progresses. Thus, prior to hardening, the composite biomaterial may be shaped and/or delivered by means of viscous flow, including such processes as percutaneous or surgical injection, channel die forging, compression molding, injection molding, extrusion, or the like. In addition, mechanical deformation during viscous flow desirably can include aligning the calcium phosphate reinforcement particles morphologically and/or crystallographically. One skilled in the art will recognize that the desired shape of the implant may be formed ex vivo by mechanical deformation prior to hardening, by shaping or machining a bulk block of the biomaterial after hardening, or by either percutaneous or surgical injection of the biomaterial to the desired locus where it will harden in vivo.

The following examples further illustrate the present invention but, of course, should not be construed as in any way limiting its scope.

Examples 1-4

Exemplary HA Whisker Syntheses

These examples demonstrate the preparation of exemplary calcium phosphate, namely calcium hydroxyapatite ($Ca_{10}(PO_4)_6(OH)_2$), reinforcement particles in the shape of "whiskers" with varied size and shape.

Homogeneous solutions containing 0.015M P, 0.025M Ca and 0.050M chelating acid were prepared. For each solution, 1.725 g of $H_3PO_4$ and a chelating acid were first added to 1000 ml distilled, de-ionized water under moderate stirring at room temperature, before dissolving 1.853 g $Ca(OH)_2$. The chelating acid was used to chelate Ca ions in solution and included one of the following: 5.124 g DL-lactic acid ($CH_3CHOHCO_2H$), 2.302 g formic acid ($HCO_2H$), 3.003 g glacial acetic acid ($CH_3CO_2H$), or 5.110 g valeric acid ($CH_3(CH_2)_3CO_2H$), which correspond to examples 1-4, respectively. Each solution was sealed to prevent evaporation and continuously stirred until the dissolution of $Ca(OH)_2$ was determined to be complete upon visual inspection (typically after 2 h). Solutions were then filtered, measured for pH, and stored in bottles purged with nitrogen gas. Each solution had pH=4. If necessary, $HNO_3$ or $NH_4OH$ were added to achieve this pH.

HA whiskers were grown by precipitation from the homogenous reaction solutions in a PTFE-lined stainless steel pressure vessel. The vessel was filled with a 100 ml aliquot of the reaction solution, purged with nitrogen gas, and sealed. The reactor was heated by placing the entire vessel into an oven equilibrated at the desired reaction temperature. The temperature inside the reactor was measured with time by a thermocouple placed inside the TEFLON® liner and was shown to asymptotically reached the ambient oven temperature. The reaction was held at a final temperature of 200° C. for 2 h (8 h total).

After reaction, the pressure vessel was removed from the oven and cooled to less than 100° C. within 1 h using a water-cooled aluminum block and motorized fan. Precipitates were filtered from the supernatant solution using a Büchner funnel and washed under a continuous flow of 100 ml distilled, de-ionized water. The filtrate was placed in a petri dish and dried in an oven at 80° C. for at least 12 h.

The precipitate was identified as calcium hydroxyapatite by x-ray diffraction (XRD). The particle dimensions and whisker morphology of the precipitates was observed by optical microscopy and quantitatively measured using stereological techniques (Table 2).

TABLE 2

Average Size and Shape Measured for the HA Whiskers Synthesized

| Example | Chelating Acid | avg. length (μm) | avg. width (μm) | avg. aspect ratio |
|---|---|---|---|---|
| 1 | DL-lactic acid | 22.3 | 2.4 | 9.5 |
| 2 | formic acid | 19.3 | 2.3 | 8.7 |
| 3 | acetic acid | 25.9 | 2.5 | 10.7 |
| 4 | valeric acid | 43.1 | 4.3 | 11.3 |

Example 5

Exemplary HA-HDPE Composites

This example demonstrates the preparation of an exemplary high density polyethylene (HDPE) matrix reinforced with calcium phosphate, namely calcium hydroxyapatite ($Ca_{10}(PO_4)_6(OH)_2$), reinforcement particles in the shape of "whiskers". For comparison, specimens were made from the HDPE polymer matrix alone as well as the HDPE polymer matrix reinforced with a conventional, equiaxed HA powder using the same processing technique.

HA whiskers were grown by precipitation from a homogenous aqueous solution (similar to example 1), containing 0.05 M $Ca(OH)_2$, 0.03 M $H_3PO_4$, and 0.10 M lactic acid, in a TEFLON® lined stainless steel pressure vessel at 200° C. for 4 h. HDPE powder was prepared by dissolving commercially available HDPE pellets in boiling xylene, cooling the solution to form a gel, extracting the solvent, and homogenizing the precipitated polymer in ethanol.

The appropriate amounts of HDPE and HA powders were ultrasonically dispersed in ethanol at a solids loading of 13 vol %. The suspension was vacuum filtered in a 10 mm diameter mold to form a porous cylindrical composite preform. After drying, the preform was subsequently pressed in a 10 mm vacuum pellet die to 280 MPa at 25° C. and again at 145° C. Apparent densities of greater than 97% were typically achieved. The densified preform was then placed vertically into a channel die forge and bilaterally extruded at 145° C. into a 2.5×10×120 mm flat bar, from which ASTM D638 type V tensile bars were machined. Tensile tests were performed under atmospheric conditions and a displacement rate of 5 mm/min.

The degree of preferred crystallographic orientation was determined by x-ray diffraction (XRD). For comparison, human cortical bone specimens were taken from the proximal end of the femoral midshaft. Thick sections were deproteinized by soaking 72 h in 7% NaOCl. The Harris texture index (see, e.g., Harris and Peterson articles, supra) was used to semi-quantitatively measure the degree of preferred crystallographic orientation (see discussion herein above).

Figure 4A:
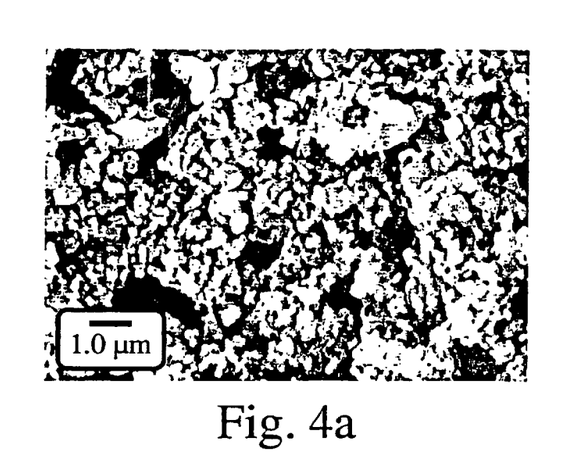
FIG. 4A illustrates a scanning election microscopy (SEM) micrograph of conventional calcium hydroxyapatite (HA) powder.
Figure 4B:
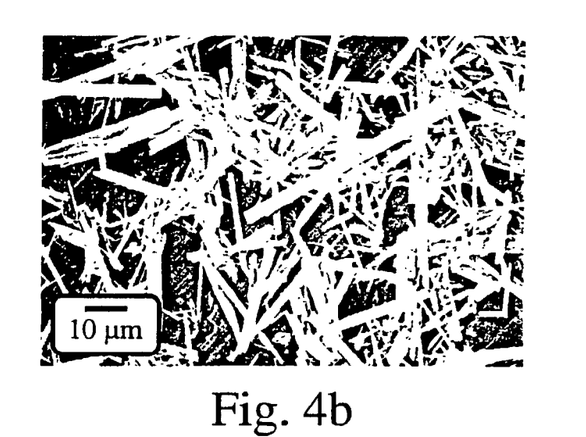
FIG. 4B illustrates an SEM micrograph of HA whiskers.
Figure 4C:
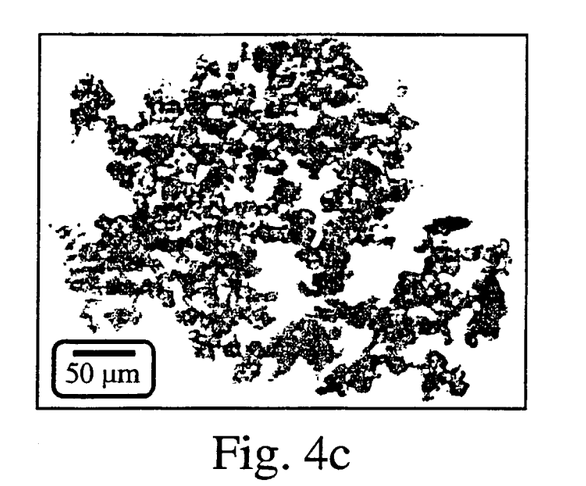
FIG. 4C illustrates an optical micrograph of high density polyethylene (HDPE) powder.

The particle size and morphology of all starting powders were observed by scanning electron microscopy (SEM), and are shown in FIGS. 4A-4C, respectively. The conventional HA (FIG. 4A) was equiaxed and spherical with an average particle size of 2-3 μm. The whiskers (FIG. 4B) were on average 20 μm in length with an average aspect ratio of 10. Note that the [002] crystallographic axis lies along the whisker length. The HDPE powder particles (FIG. 4C) were spherical and 10-30 μm in diameter.

Figure 5A:
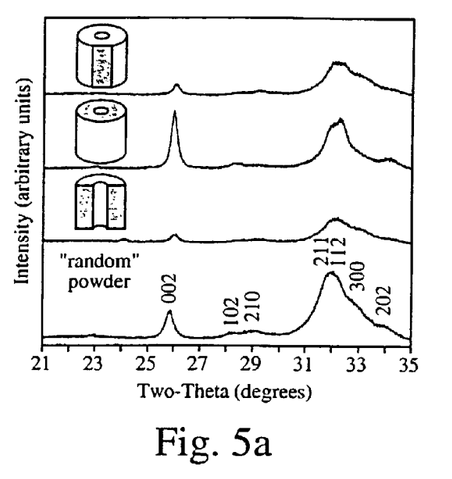
FIG. 5A illustrates x-ray diffraction patterns (XRD) of HA crystals in a human cortical bone (femoral midshaft) specimen.
Figure 5B:
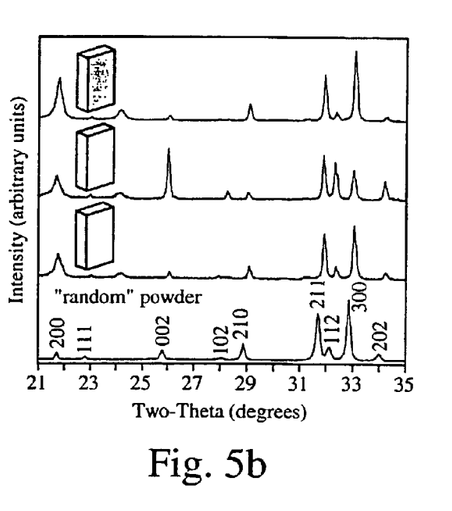
FIG. 5B illustrates XRD patterns for HA crystals in an exemplary synthetic HDPE-HA composite that includes 30% by volume HA.
Figure 6A:
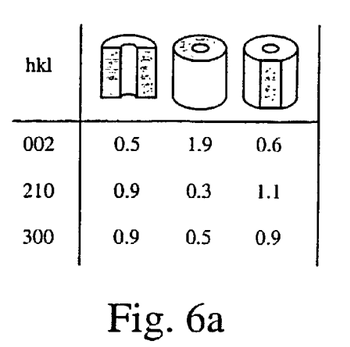
FIG. 6A illustrates Harris texture index measurements of HA crystals in a human cortical bone (femoral midshaft) specimen.
Figure 6B:
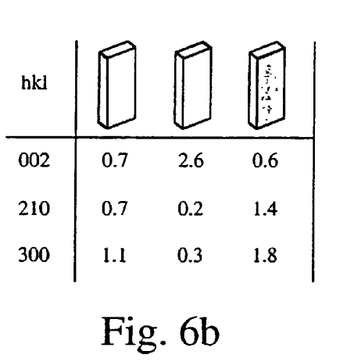
FIG. 6B illustrates Harris texture index measurements of HA crystals in an exemplary synthetic HDPE-HA composite that includes 30% by volume HA.

XRD patterns for human cortical bone specimens and an exemplary composite are shown in FIGS. 5A and 5B. In both cases, the (002) peaks have a higher relative intensity on the longitudinal cross-sections (second pattern from top) than on the perpendicular cross-sections (the patterns above and below). Thus, HA crystals in both specimens have a preferred orientation in the longitudinal directions (vertical in the schematics). Harris texture index measurements provided a semi-quantitative estimate the degree of preferred orientation and are shown in FIGS. 6A and 6B. As will be appreciated by those of ordinary skill in the art, in FIGS. 6A and 6B, "hkl" corresponds to the Miller indices of specific crystallographic planes of the HA reinforcement particles. It is to be noted that each crystallographic plane listed in FIG. 6 (002, 210, 300) corresponds to a specific XRD peak in FIG. 5. It also is to be noted that a value of 1.0 corresponds to a random orientation distribution. Under the given processing conditions, a slightly higher but similar degree of preferred orientation was achieved in the synthetic composite compared to cortical bone. The preferred orientation in bone is known to be physiological in origin. In the HDPE-HA composite, whisker alignment was induced by shear stresses occurring along the flow field as the material extruded in the forge mold.

Mechanical tests demonstrated the improved mechanical properties of the HA whisker reinforced composites compared to the matrix alone as well as reinforcement with a conventional HA powder (Table 3). The enhanced mechanical properties over the conventional HA powder are attributed to the anisometric morphology of the whisker reinforcements and their preferred orientation ("alignment") along the direction of applied stress.

TABLE 3

Mechanical Properties of the Composites in Example 5

| vol % HA | Reinforcement Phase | Ultimate Tensile Strength (MPa) | Tensile Modulus (GPa) |
|---|---|---|---|
| 0 | none | 27 | 1.1 |
| 10 | conventional HA | 27 | 2.2 |
| 10 | HA whiskers | 27 | 2.5 |
| 30 | conventional HA | 23 | 5.3 |
| 30 | HA whiskers | 28 | 6.5 |

Example 6

Exemplary HA-PMMA Bone Cement Composites

This example demonstrates the preparation of an exemplary poly(methylmethacrylate) (PMMA) matrix reinforced with calcium phosphate, namely calcium hydroxyapatite ($Ca_{10}(PO_4)_6(OH)_2$), reinforcement particles in the shape of "whiskers". For comparison, specimens were made from the PMMA polymer matrix alone as well as the PMMA polymer matrix reinforced with a conventional, equiaxed HA powder using the same processing technique.

HA whiskers were grown by precipitation from a homogenous aqueous solution (similar to example 1), containing 0.05 M $Ca(OH)_2$, 0.03 M $H_3PO_4$, and 0.10 M lactic acid, in a Teflon lined stainless steel pressure vessel at 200° C. for 2 h. A commercially available PMMA bone cement, Simplex P™ (Howmedica), was mixed according to manufacturer recommendations using a vacuum stirring bowl. However, the monomer and powder ratios were adjusted to accommodate incorporating varying volume fractions of the HA reinforcements. Prior to reaching the "dough" stage, the bone cements were added to a syringe and injected into ASTM D638 type V tensile specimen mold or into ASTM F571 compression specimen molds. All tests were performed under atmospheric conditions and a displacement rate of 5 mm/min.

The particle size and morphology of the HA reinforcement powders were observed by scanning electron microscopy (SEM), and are shown in FIG. 5. The conventional HA was equiaxed and spherical with an average particle size of 2-3 µm. The whiskers were on average 20 µm in length with an average aspect ratio of 10. Note that the [002] crystallographic axis lies along the whisker length.

Mechanical tests demonstrated the improved mechanical properties of the HA whisker reinforced composites compared to the matrix alone as well as reinforcement with a conventional HA powder (Table 4). The enhanced mechanical properties over the conventional HA powder are attributed to the anisometric morphology of the whisker reinforcements and their preferred orientation ("alignment") along the direction of applied stress. Shear stresses caused by material flow during injection developed a preferred crystallographic orientation of the HA whiskers within the matrix material and yielded anisotropic mechanical properties. The degree of preferred orientation in HA whisker reinforced specimens, like example 5, was similar to that measured in human cortical bone.

TABLE 4

Mechanical Properties of the Composites in Example 6.

| vol % HA | Reinforcement Phase | Ultimate Tensile Strength (MPa) | Tensile Modulus (GPa) | Ultimate Compressive Strength (MPa) |
|---|---|---|---|---|
| 0 | none | 37 | 3.0 | 129 |
| 10 | conventional HA | 23 | 3.5 | 117 |
| 10 | HA whiskers | 27 | 4.3 | 125 |

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A composite biomaterial comprising:
    (a) a matrix including
        (i) a calcium phosphate composition that can cure in vivo,
        (ii) a thermoplastic polymer, or
        (iii) any combination of (i) and/or (ii); and
    (b) anisometric calcium phosphate reinforcement particles dispersed within the matrix,
    wherein the reinforcement particles are aligned within the matrix and are present in an amount of from about 1% by volume of the composite to about 60% by volume of the composite, and
    wherein the reinforcement particles have a mean aspect ratio (length along c-axis/length along a-axis) of greater than 1 and less than 100.

2. The composite of claim 1, wherein the mean aspect ratio is from about 5 to about 50.

3. The composite of claim 2, wherein the mean aspect ratio is from about 10 to about 20.

4. The composite of claim 1, wherein at least some of the reinforcement particles are shaped like whiskers.

5. The composite of claim 1, wherein at least some of the reinforcement particles are shaped like platelets.

6. The composite of claim 1, wherein the reinforcement particles are present in an amount of from about 40% by volume of the composite to about 60% by volume of the composite.

7. The composite of claim 1, wherein the reinforcement particles have dimensions of from about 1 micrometer to about 500 micrometers along the c-axis and from about 0.02 micrometers to about 20 micrometers along the a-axis.

8. The composite of claim 7, wherein the reinforcement particles have a length of from about 5 micrometers to about 50 micrometers along the c-axis and from about 0.1 micrometers to about 10 micrometers along the a-axis.

9. The composite of claim 1, wherein the matrix includes at least one thermoplastic that is non-bioresorbable.

10. The composite of claim 9, wherein the non-bioresorbable thermoplastic is selected from the group consisting of polyethylene, high density polyethylene (HDPE), ultra high molecular weight polyethylene (UHMWPE), low density polyethylene (LDPE), polybutylene, polystyrene, polyurethane, polyacrylates, polymethacrylates, polypropylene, copolymers thereof, and blends thereof.

11. The composite of claim 1, wherein the matrix includes at least one thermoplastic that is bioresorbable.

12. The composite of claim 11, wherein the bioresorbable thermoplastic is selected from the group consisting of poly (DL-lactide) (DLPLA), poly(L-lactide) (LPLA), poly(glycolide) (PGA), poly(e-caprolactone) (PCL), poly(dioxanone) (PDO), poly(glyconate), poly(hydroxybutyrate) (PHB), poly (hydroxyvalerate (PHV), poly(orthoesters), poly(carboxylates), poly(propylene fumarate), poly(phosphates), poly (carbonates), poly(anhydrides), poly(iminocarbonates), poly (phosphazenes), copolymers or blends thereof, and combinations thereof.

13. The composite of claim 1, wherein the composite includes at least one non-bioresorbable thermoplastic and at least one bioresorbable thermoplastic.

14. The composite of claim 13, wherein the bioresorbable thermoplastic is graded from a surface of the matrix to an inner core of the matrix.

15. The composite of claim 1, wherein the matrix includes at least one calcium phosphate compound.

16. The composite of claim 15, wherein the matrix includes particulate or dissolved bioresorbable or non-bioresorbable thermoplastic.

17. The composite of claim 1, wherein at least some of the reinforcement particles are bioresorbable.

18. The composite of claim 17, wherein the bioresorbable reinforcement particles are graded from a surface of the matrix to an inner core of the matrix.

19. The composite of claim 1, wherein the matrix includes the calcium phosphate composition, and wherein the calcium phosphate composition is selected from the group consisting of amorphous calcium phosphate, biphasic calcium phosphate, calcium phosphate, dicalcium phosphate, dicalcium phosphate dihydrate, calcium hydroxyapatite, carbonated calcium hydroxyapatite, monocalcium phosphate, monocalcium phosphate monohydrate, octacalcium phosphate, tricalcium phosphate, alpha-tricalcium phosphate, beta-tricalcium phosphate, tetracalcium phosphate, and combinations thereof.

20. The composite of claim 19, wherein the calcium phosphate composition includes at least one dopant.

21. The composite of claim 1, wherein the anisometric calcium phosphate reinforcement particles are selected from the group consisting of amorphous calcium phosphate, biphasic calcium phosphate, calcium phosphate, dicalcium phosphate, dicalcium phosphate dihydrate, calcium hydroxyapatite, carbonated calcium hydroxyapatite, monocalcium phosphate, monocalcium phosphate monohydrate, octacalcium phosphate, tricalcium phosphate, alpha-tricalcium phosphate, beta-tricalcium phosphate, tetracalcium phosphate, and combinations thereof.

22. The composite of claim 21, wherein at least some of the anisometric calcium phosphate reinforcement particles include at least one dopant.

23. The composite of claim 1, further comprising at least one surface-active agent.

24. The composite of claim 1, further comprising at least one additive selected from the group consisting of growth factors, transcription factors, matrix metalloproteinases, peptides, proteins, and combinations thereof.

25. A prosthesis for replacement of bone comprising the composite of claim 1.

26. A method of preparing the composite biomaterial of claim 1, the biomaterial comprising:
   (a) a matrix including at least one thermoplastic polymer and
   (b) anisometric calcium phosphate reinforcement particles arranged within the matrix, said method comprising:
      providing the anisometric calcium phosphate reinforcement particles;
      providing the polymer;
      co-processing the polymer and the calcium phosphate reinforcement particles to obtain a substantially uniform mixture thereof; and
      thermo-mechanically or mechanically deforming and/or densifying the mixture to faun the composite biomaterial.

27. The method of claim 26, wherein the anisometric calcium phosphate reinforcement particles are provided via a hydrothermal reaction.

28. The method of claim 26,
   wherein said providing the polymer includes providing particles of the polymer in a first suspension,
   wherein said providing the anisometric calcium phosphate reinforcement particles includes providing the reinforcement particles
      (a) in the first suspension or
      (b) in a second suspension, and
   wherein said co-processing the polymer and the calcium phosphate reinforcement particles to obtain a substantially uniform mixture thereof comprises wet co-consolidating the calcium phosphate reinforcement particles and the polymer particles.

29. The method of claim 28, wherein the polymer particles are produced by dissolving the polymer in a solvent under mixing, followed by precipitation or gelation of the polymer from the solution, followed by solvent removal.

30. The method of claim 29, wherein the solvent removal is by way of vacuum oven drying, distillation and collection, or freeze drying.

31. The method of claim 26, wherein said providing the polymer includes providing a foam of polymer having continuous open porosity, and wherein said co-processing includes infiltrating the polymer foam with a suspension of the calcium phosphate reinforcement particles to form a preform.

32. The method of claim 31, wherein the polymer foam is produced by dissolving the polymer in a solvent under mixing, followed by precipitation or gelation of the polymer from the solution, followed by solvent removal.

33. The method of claim 32, wherein the solvent removal is by way of vacuum oven drying, distillation and collection, or freeze drying.

34. The method of claim 26, wherein said providing the anisometric calcium phosphate reinforcement particles includes providing a porous compact of the calcium phosphate reinforcement particles, wherein said providing the polymer includes providing a molten or solvated polymer or as a polymerizing mixture comprising monomer and initiator, and, optionally polymer powder, co-initator, and/or stabilizer, and wherein said co-processing includes infiltrating the porous compact of the calcium phosphate reinforcement particles with the polymer.

35. The method of claim 34, wherein the porous compact of the calcium phosphate reinforcement particles is produced by dry pressing calcium phosphate particles and sintering the dry pressed particles to form the compact.

36. The method of claim 35, wherein the sintering is at a temperature of from about 600° C. to about 1000° C.

37. The method of claim 26, wherein said providing the polymer includes mixing monomer with an initiator, and, optionally, polymer powder and co-initiator, to form a polymer-forming mixture, and wherein said co-processing includes polymerizing and hardening the mixture in situ.

38. The method of claim 37, wherein said initiator and/or co-initiator is selected from the group consisting of benzoyl peroxide, dimethylaniline, ascorbic acid, cumene hyperoxide, tributylborane, sulfinic acid, 4-cyanovaleric acid, potassium persulfate, dimethoxybenzoine, benzoic-acid-phenylester, N,N-dimethyl p-toluidine, dihydroxy-ethyl-p-toluidinebenzoyl peroxide, and any combination thereof.

39. The method of claim 37, wherein said monomer is selected from the group consisting of methylmethacrylate (MMA), 2,2'-bis(methacryloylethoxyphenyl) propane (bis-MEEP), bisphenol a polyethylene glycol diether dimethacrylate (bis-EMA), urethane dimethacrylate (UDMA), diphenyloxymethacrylate (DPMA), n-butylmethacrylate, tri (ethylene glycol) dimethacrylate (TEG-DMA), bisphenol a hydroxypropylmethacrylate (bis-GMA), and any combination thereof.

40. The method of claim 37, wherein said providing the polymer includes adding a stabilizer to prevent premature polymerization of the polymer.

41. The method of claim 40, wherein said stabilizer is selected from hydroquinone, 2-hydroxy-4-methoxy-benzophenone, or combinations thereof.

42. The method of claim 37, wherein said co-processing comprises combining said anisometric calcium phosphate reinforcement particles with said polymer-forming mixture prior to mixing the components thereof.

43. The method of claim 37, wherein said co-processing comprises combining said anisometric calcium phosphate reinforcement particles with said polymer-forming mixture during polymerization.

44. The method of claim 26, wherein the deforming and/or densifying includes aligning the calcium phosphate reinforcement particles morphologically and/or crystallographically.

45. The method of claim 26, wherein the thermo-mechanically deforming and/or densifying includes channel die forging.

46. The method of claim 26, wherein the thermo-mechanically or mechanically deforming and/or densifying includes compression molding or die pressing.

47. The method of claim 26, wherein the thermo-mechanically deforming and/or densifying includes injection molding.

48. The method of claim 26, wherein the thermo-mechanically deforming and/or densifying includes extrusion or pultrusion.

49. The method of claim 26, wherein the mechanically deforming and/or densifying includes the viscous flow of a molten or polymerizing polymer matrix.

50. The method of claim 49, wherein the viscous flow is achieved by percutaneous or surgical injection, channel die forging, compression molding, injection molding, or extrusion.

51. The method of claim 26, further comprising adding a surface-active agent.

52. The composite of claim 1, wherein the reinforcement particles are aligned in the matrix such that they have an orientation distribution function (ODF) of greater than 1 MRD.

53. The composite of claim 52, wherein the reinforcement particles are aligned in the matrix such that they have an orientation distribution function (ODF) of at least about 3 MRD.

54. The composite of claim 53, wherein the reinforcement particles are aligned in the matrix such that they have an orientation distribution function (ODF) of about 5 MRD to about 20 MRD.

55. A composite biomaterial comprising:
(a) a matrix including
(i) a calcium phosphate composition that can cure in vivo,
(ii) a thermoplastic polymer, or
(iii) any combination of (i) and/or (ii); and
(b) anisometric calcium phosphate reinforcement particles dispersed within the matrix,
wherein the reinforcement particles are aligned within the matrix and have an orientation distribution function (ODF) of greater than 1 MRD, and
wherein the reinforcement particles have a mean aspect ratio (length along c-axis/length along a-axis) of greater than 1 and less than 100.

56. The composite of claim 55, wherein the mean aspect ratio is from about 5 to about 50.

57. The composite of claim 55, wherein at least some of the reinforcement particles are shaped like whiskers.

58. The composite of claim 55, wherein at least some of the reinforcement particles are shaped like platelets.

59. The composite of claim 55, wherein the reinforcement particles are present in an amount of from about 1% by volume of the composite to about 60% by volume of the composite.

60. The composite of claim 55, wherein the reinforcement particles have dimensions of from about 1 micrometer to about 500 micrometers along the c-axis and from about 0.02 micrometers to about 20 micrometers along the a-axis.

61. The composite of claim 55, wherein the anisometric calcium phosphate reinforcement particles are selected from the group consisting of amorphous calcium phosphate, biphasic calcium phosphate, calcium phosphate, dicalcium phosphate, dicalcium phosphate dihydrate, calcium hydroxyapatite, carbonated calcium hydroxyapatite, monocalcium phosphate, monocalcium phosphate monohydrate, octacalcium phosphate, tricalcium phosphate, alpha-tricalcium phosphate, beta-tricalcium phosphate, tetracalcium phosphate, and combinations thereof.

62. The composite of claim 55, further comprising at least one additive selected from the group consisting of growth factors, transcription factors, matrix metalloproteinases, peptides, proteins, and combinations thereof.

63. A prosthesis for replacement of bone comprising the composite of claim 55.

64. A method of preparing the composite biomaterial of claim 55, the biomaterial comprising:
   (a) a matrix including at least one thermoplastic polymer and
   (b) anisometric calcium phosphate reinforcement particles arranged within the matrix, said method comprising:
      providing the anisometric calcium phosphate reinforcement particles;
      providing the polymer;
      co-processing the polymer and the calcium phosphate reinforcement particles to obtain a substantially uniform mixture thereof; and
      thermo-mechanically or mechanically deforming and/or densifying the mixture to form the composite biomaterial.

65. The method of claim 64,
   wherein said providing the polymer includes providing particles of the polymer in a first suspension,
   wherein said providing the anisometric calcium phosphate reinforcement particles includes providing the reinforcement particles
      (a) in the first suspension or
      (b) in a second suspension, and
   wherein said co-processing the polymer and the calcium phosphate reinforcement particles to obtain a substantially uniform mixture thereof comprises wet co-consolidating the calcium phosphate reinforcement particles and the polymer particles.

* * * * *